United States Patent
Knudsen et al.

(10) Patent No.: US 6,939,853 B2
(45) Date of Patent: Sep. 6, 2005

(54) COMBINED USE OF A GLP-1 COMPOUND AND ANOTHER DRUG FOR TREATING DYSLIPIDEMIA

(75) Inventors: Lotte Bjerre Knudsen, Valby (DK); Johan Selmer, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/328,284

(22) Filed: Dec. 23, 2002

(65) Prior Publication Data

US 2003/0143183 A1 Jul. 31, 2003

Related U.S. Application Data

(60) Provisional application No. 60/350,088, filed on Jan. 17, 2002.

(30) Foreign Application Priority Data

Dec. 29, 2001 (DK) .......................... 2001 01970
May 17, 2002 (DK) .......................... 2002 00759

(51) Int. Cl.⁷ .......................... A61K 38/16; C07K 14/00
(52) U.S. Cl. .......................... 514/12; 530/324
(58) Field of Search .......................... 530/324; 514/12, 514/21

(56) References Cited

U.S. PATENT DOCUMENTS

| | | | | |
|---|---|---|---|---|
| 5,264,455 A | * | 11/1993 | Varma et al. | 514/459 |
| 5,919,818 A | * | 7/1999 | Lane et al. | 514/458 |
| 6,150,413 A | | 11/2000 | Bernardon et al. | 514/568 |
| 6,214,820 B1 | | 4/2001 | Jeppesen et al. | 514/211.11 |
| 6,458,851 B1 | * | 10/2002 | Keller et al. | 514/655 |
| 2002/0187926 A1 | * | 12/2002 | Knudsen et al. | 514/2 |
| 2003/0022816 A1 | * | 1/2003 | Knudsen et al. | 514/2 |
| 2003/0040469 A1 | * | 2/2003 | Knudsen | 514/12 |
| 2003/0199451 A1 | * | 10/2003 | Mogensen et al. | 514/12 |

FOREIGN PATENT DOCUMENTS

| | | |
|---|---|---|
| EP | 0551035 A1 | 7/1993 |
| EP | 0879814 A1 | 11/1998 |
| EP | 0903343 A1 | 3/1999 |
| WO | WO 94/01420 | 1/1994 |
| WO | WO 95/03313 | 2/1995 |
| WO | WO 96/04260 | 2/1996 |
| WO | WO 96/04261 | 2/1996 |
| WO | WO 97/25042 | 7/1997 |
| WO | WO 97/36579 | 10/1997 |
| WO | WO 98/05331 | 2/1998 |
| WO | 98/08871 | 3/1998 |
| WO | WO 98/30231 A1 * | 7/1998 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38501 | 8/1999 |
| WO | WO 99/38850 | 8/1999 |
| WO | 99/43706 | 9/1999 |
| WO | 99/43708 | 9/1999 |
| WO | WO 99/62872 | 12/1999 |
| WO | WO 00/00195 | 1/2000 |
| WO | 00/66629 | 11/2000 |
| WO | 01/04146 | 1/2001 |
| WO | 01/04156 | 1/2001 |
| WO | 01/27128 | 4/2001 |
| WO | 01/66135 | 9/2001 |
| WO | 01/94293 | 12/2001 |

OTHER PUBLICATIONS

Hiyoshi et al. Squalene synthase inhibitors reduce plasma triglyceride ... European Journal of Pharmacology. vol. 431, pp. 345–352 (Nov. 23, 2001).*
Ugawa et al., British Journal of Pharmacology, vol. 131, no. 1 (2000), pp. 63–70.
Higaki et. al., Arteriosclerosis, Thrombosis And Vascular Biology, vol. 18, No. 8, (1998), pp. 1304–1311.
C. Orskov, Diabetologia, vol. 35, pp. 701–711 (1992).
Kronenberg et al., Critical Reviews in Clinical Laboratory Sciences, vol. 33, pp. 495–543 (1996).
Frick, M.D. et al., The New England Journal of Medicine, vol. 317, pp. 1237–1245 (1987).
Uusitupa, M.D. et al., Circulation, vol. 82, pp. 27–36 (1990).
The Lancet, vol. 344, pp. 1383–1389 (1994).
Griffin et al., Atherosclerosis, vol. 106, pp. 241–253 (1994).
Juntti–Berggren, M.D., Ph.D. et al., Diabetes Care, vol. 19, pp. 1200–1206 (1996).
Creutzfeldt, M.D., F.R.C.P. et al., Diabetes Care, vol. 19, pp. 580–586 (1996).
Toft–Nielsen, M.D. et al., Diabetes Care, vol. 22, pp. 1137–1143 (1999).
Abstract of Kolterman et al., Diabetologia, Supplement 1, vol. 43, p. A189 (2000).
Young et al., Diabetes, (1999), vol. 48, pp. 1026–1034.

* cited by examiner

*Primary Examiner*—Jeffrey Edwin Russel
(74) *Attorney, Agent, or Firm*—Richard W. Bork, Esq.; Reza Green, Esq.; Rosemarie R. Wilk-Orescan, Esq.

(57) ABSTRACT

Methods and uses for treatment of dyslipidemia comprising administration of a GLP-1 compound and another antidyslipidemic drug.

2 Claims, No Drawings

COMBINED USE OF A GLP-1 COMPOUND AND ANOTHER DRUG FOR TREATING DYSLIPIDEMIA

CROSS REFERENCE TO RELATED APPLICATIONS

The present application claims the benefit under 35 U.S.C. 119 of Danish applications PA 2001 01970 and PA 2002 00759 filed Dec. 29, 2001 and May 17, 2002 respectively, and of U.S. provisional application 60/350,088, filed Jan. 17, 2002, the contents of which are hereby incorporated by reference.

FIELD OF THE INVENTION

The present invention relates to methods for treatment and/or prevention of dyslipidemia. More specifically, the methods and uses of the invention pertains to administration of a GLP-1 compound in combination with administration of another antidyslipidemic agent.

BACKGROUND OF THE INVENTION

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterised as type 1 diabetes and insufficient utilization of insulin is type 2 diabetes.

Dyslipidemia, or abnormal levels of lipoproteins in serum, is a frequent occurrence among diabetics. In type 1 diabetes with optimal glycaemic control the concentrations of serum lipoproteins are typically characterized by normal to subnormal very low density lipoprotein (VLDL), elevated high density lipoprotein (HDL) cholesterol and normal to subnormal low density lipoprotein (LDL) cholesterol. Lipoprotein profile in type 1 diabetic patients with good glycaemic control is not atherogenic. In fact, it seems antiatherogenic although lack of lipoprotein abnormalities does not exclude the possibility that certain compositional alterations may be potentially atherogenic. In type 1 diabetics with poor glycaemic control the serum concentration of lipoproteins are typically characterized by increased VLDL, reduced HDL cholesterol and increased LDL cholesterol. This profile is atherogenic but it may be corrected by intensive insulin treatment of the patient to reach a state of good glycaemic control.

In type 2 diabetes abnormalities of serum lipids and lipoproteins are much more frequent than in type 1 diabetes. Dyslipidemia in type 2 diabetes is typically characterized by elevated serum and VLDL triglycerides, low HDL cholesterol, normal to elevated levels of LDL cholesterol and increased levels of small dense, LDL particles in the blood. Serum and VLDL triglycerides are usually 1.5–3 times higher in type 2 diabetics as compared to non-diabetic controls with matched body mass index, age and sex. Regardless of the mode of treatment of type 2 diabetes, the characteristic lipoprotein profile is atherogenic. Furthermore, the excessive postprandial lipaemia is positively correlated with fasting serum triglyceride levels in type 2 diabetics. Taken together these abnormalities are significant risk factors not only for coronary heart disease but also for the progression of coronary artery disease.

Dyslipidemia is one of the main contributors to the increased incidence of coronary events and deaths among diabetic subjects. Several epidemiological studies have confirmed this by showing a several-fold increase in coronary deaths among diabetic subjects when compared with non-diabetic subjects. Although the lipid profiles in type 1 diabetes and in type 2 diabetes both exhibit potentially atherogenic features, the lipoprotein profile in type 2 diabetes is atherogenic regardless of the mode of treatment. In type 2 diabetes the problem is of immense proportions since the majority of the patients have atherogenic dyslipidemia. In terms of atherogenic potential, dyslipidemia is comparable to hypercholesterolemia. Therefore, to relieve this burden accompanying diabetes new therapeutic approaches are needed.

Several drugs are being used in the treatment of dyslipidemia. The drugs can intervene by lowering cholesterol (LDL and total cholesterol) or by lowering triglyceride levels in plasma. Treatment of hyperlipidemia using statins or PPAR/LXR modulating compounds such as fibric acid derivatives have been used to lower serum levels of cholesterol and triglyceride. Statins such as atorvastatin, lovastatin, fluvastatin, simvastatin and pravastatin are HMG CoA reductase inhibitors which act by inhibiting cholesterol synthesis and upregulate LDL receptors in liver. Statins are used to treat elevated LDL, and common side effects are myositis, arthralgias, gastrointestinal upset and elevated liver function tests. The fibric acid derivatives e.g. clofibrate, gemfibrozil, fenofibrate and ciprofibrate, stimulate lipoprotein lipase that breaks down lipids in lipoproteins and may decrease VLDL synthesis. Fibric acid derivatives are used to treat elevated triglyceride levels and among the side effects are myositis, gastrointestinal upset, gallstones and elevated liver function tests. Other drug types used for treatment of hyperlipidemia are bile acid binding resins (bile acid sequestrants), e.g. cholestyramine and cholestipol, with the major indication being elevated LDL. Bile acid binding resins promote bile acid excretion and they increase LDL receptors in the liver. Common side effects are bloating, constipation and elevated triglycerides. Nicotinic acid decreases VLDL synthesis and is used for treatment of elevated LDL and VLDL. Among the side effects of nicotinic acid are cutaneous flushing, gastrointestinal upset, elevated glucose, uric acid and liver function tests. Thus, there is a need for the therapeutic benefits of several anti-dyslipidemic drugs while simultaneously reducing the severe side effects.

Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. Processing of preproglucagon to give GLP-1 (7–36)amide, GLP-1(7–37) and GLP-2 occurs mainly in the L-cells. A simple system is used to describe fragments and analogues of this peptide. Thus, for example, $Gly^8$-GLP-1 (7–37) designates a fragment of GLP-1 formally derived from GLP-1 by deleting the amino acid residues Nos. 1 to 6 and substituting the naturally occurring amino acid residue in position 8 (Ala) by Gly. Similarly, $Lys^{34}(N^\epsilon$-tetradecanoyl)-GLP-1(7–37) designates GLP-1(7–37) wherein the $\epsilon$-amino group of the Lys residue in position 34 has been tetradecanoylated. PCT publications WO 98/08871 and WO 99/43706 disclose derivatives of GLP-1 analogs, which have a lipophilic substituent. These stable derivatives of GLP-1 analogs have a protracted profile of action compared to the corresponding GLP-1 analogs. In addition to a number of other desirable effects, GLP-1 compounds have also been shown to lower plasma levels of triglycerides and cholesterol (WO 2001/66135).

A number of structural analogs of GLP-1 were isolated from the venom of the Gila monster lizards (*Heloderma suspectum* and *Heloderma horridum*). Exendin-4 is a 39 amino acid residue peptide isolated from the venom of *Heloderma horridum*, and this peptide shares 52% homology with GLP-1. Exendin-4 is a potent GLP-1 receptor agonist which has been shown to stimulate insulin release and ensuing lowering of the blood glucose level when injected into dogs. Exendin-4, exendin-4 analogs and derivatives of any of these as well as methods for production thereof can be found in WO 99/43708, WO 00/66629, and WO 01/04156. The group of GLP-1(1–37), exendin-4 (1–39), analogs thereof and derivatives thereof, (hereinafter designated GLP-1 compounds) are potent insulinotropic agents.

SUMMARY OF THE INVENTION

The present invention relates to the use of a GLP-1 compound in combination with another antidyslipidemic drug to treat dyslipidemia in diabetics and non-diabetics. This combined treatment conveys the benefits of both compounds while reducing side effects associated with each compound.

In accordance with the present invention, a pharmaceutical combination is provided for use in treatment of dyslipidemia in diabetics and in non-diabetics, which combination comprises a GLP-1 compound and another antidyslipidemic drug.

One object of the present invention is to provide methods, which can effectively be used in the treatment or prophylaxis of dyslipidemia, hyperlipoproteinemia, hypertriglyceridemia, hyperlipidemia or hypercholesterolemia.

The invention includes a method for the treatment or prophylaxis of dyslipidemia, hyperlipoproteinemia, hypertriglyceridemia, hyperlipidemia or hypercholesterolemia, which method comprises administration of a GLP-1 compound and an antidyslipidemic drug to a patient in need thereof.

In one embodiment of the invention, the GLP-1 compound is a stable derivative of a GLP-1 analog. A preferred embodiment is a GLP-1 analog with a lipophilic substituent, preferably $Arg^{34}$, $Lys^{26}(N^{\epsilon}-(\gamma-Glu(N^{\alpha}-hexadecanoyl)))$-GLP-1(7–37).

In other embodiments of the invention the antidyslipidemic drug is a statin, a squalene synthase inhibitor, a bile acid binding resin or an IBAT inhibitor.

In yet another embodiment of the invention the antidyslipidemic drug and the GLP-1 compound are administered in suboptimal dosages. In yet another embodiment of the invention the antidyslipidemic drug and the GLP-1 compound are administered in amounts and for a sufficient time to produce a synergistic effect.

DEFINITIONS

Co-administration: In the context of the present application, co-administration of two compounds is defined as administration of the two compounds to the patient within 24 hours, including separate administration of two medicaments each containing one of the compounds as well as simultaneous administration whether or not the two compounds are combined in one formulation or whether they are in two separate formulations.

Effective dosage: An effective dosage is a dosage which is sufficient in order for the treatment of the patient to be effective.

GLP-1 compound: A GLP-1 analog or a derivative thereof or exendin-4, an exendin-4 analog or a derivative thereof. For example, $Gly^{8}$-GLP-1(7–37) designates a fragment of GLP-1 formally derived from GLP-1 by deleting the amino acid residues Nos. 1 to 6 and substituting the naturally occurring amino acid residue in position 8 (Ala) by Gly. Examples of derivatives of GLP-1 analogs can be found in WO 98/08871 and WO 99/43706. Likewise, exendin-4 and analogs and derivatives thereof are described in WO 99/43708, WO 00/66629 and WO 01/04146. In the present application an analog of a parent protein means a protein wherein one or more amino acid residues of the parent protein have been substituted by other amino acid residues and/or wherein one or more amino acid residues of the parent protein have been deleted and/or wherein one or more amino acid residues have been inserted into the parent protein. Such an insertion of amino acid residues can take place at the C-terminal, at the N-terminal, within the peptide sequence or a combination thereof. In the present application the term "derivative" means a chemical derivative of the parent protein, i.e. a protein wherein at least one of the constituent amino acid residues are covalently modified. Examples of such covalent modifications are acylations, alkylations, esterifications, glycosylations and PEGylations.

Medicament: Pharmaceutical composition suitable for administration of the pharmaceutically active compound to a patient.

Suboptimal dosage: A suboptimal dosage of a pharmaceutically active compound is a dosage which is below the optimal dosage for that compound when used in single-compound therapy.

Synergistic effect: A synergistic effect of two compounds is in terms of statistical analysis an effect which is greater than the additive effect which results from the sum of the effects of the two individual compounds.

Treatment: In this application treatment is defined as the management and care of a patient for the purpose of combating the disease, condition, or disorder and includes the administration of the active compounds to prevent the onset of the symptoms or complications, or alleviating the symptoms or complications, or eliminating the disease, condition, or disorder.

Stable derivative of a GLP-1 analog: A GLP-1 analog or a derivative thereof which exhibits an in vivo plasma elimination half-life of at least 10 hours in man, as determined by the method described below. Examples of stable derivatives of GLP-1 analogs can be found in WO 98/08871 and WO 99/43706. The method for determination of plasma elimination half-life of a compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

DETAILED DESCRIPTION OF THE INVENTION

It is believed that in the treatment of dyslipidemia the combined treatment with a GLP-1 compound and another antidyslipidemic drug provides a favourable effect with a minimum of side effects as compared to single compound therapy.

A synergistic effect of two compounds permits the dosages of these compounds in the combined treatment to be below the optimal dosages of the individual compounds in single-compound treatment. Thus, these suboptimal dosages of the individual compounds reduce side effects since lower dosages are needed for the same therapeutic effect in the combined treatment.

Accordingly, the present invention relates to methods for treatment of dyslipidemia, hyperlipoproteinemia, hypertriglyceridemia, hyperlipidemia or hypercholesterolemia, which method comprises administration of a GLP-1 compound and another antidyslipidemic drug to a patient in need thereof.

The methods comprise administration of an effective amount of a GLP-1 compound and administration of an effective amount of another antidyslipidemic drug. The two compounds may be co-administered or they may be administered separately as two medicaments. Furthermore, the first compound may be administered in a regimen, which additionally comprises treatment with the second compound. Hence, according to the present invention the only provision is that there must be overlapping periods of treatment with the GLP-1 compound and the other antidyslipidemic drug.

In one embodiment of the invention, the GLP-1 compound is a stable derivative of a GLP-1 analog. A preferred embodiment is a GLP-1 analog with a lipophilic substituent, preferably $Arg^{34}$, $Lys^{26}(N^{\epsilon}-(\gamma-Glu(N^{\alpha}-hexadecanoyl)))$-GLP-1(7–37). $Arg^{34}$, $Lys^{26}(N^{\epsilon}-(\gamma-Glu(N^{\alpha}-hexadecanoyl)))$-GLP-1(7–37) is disclosed in WO 98/08871. In another embodiment of the invention, the GLP-1 compound is exendin-4 or an analog or derivative thereof.

In another embodiment of the invention, the GLP-1 compound is an analog of GLP-1(7–37) which has less than 10 amino acid residues different from those in GLP-1(7–37), less than 5 amino acid residues different from those in GLP-1(7–37), less than 3 amino acid residues different from those in GLP-1(7–37), preferably only one amino acid residue different from that in GLP-1(7–37).

In another embodiment of the invention, the GLP-1 compound is selected from the group consisting of $Gly^8$-GLP-1(7–36)-amide, $Gly^8$-GLP-1(7–37), $Val^8$-GLP-1(7–36)-amide, $Val^8$-GLP-1(7–37), $Val^8Asp^{22}$-GLP-1(7–36)-amide, $Val^8Asp^{22}$-GLP-1(7–36) $Val^8Glu^{22}$-GLP-1(7–36)-amide, $Val^8Glu^{22}$-GLP-1(7–37)-amide, $Val^8Lys^{22}$-GLP-1(7–3)-amide, $Val^8Lys^{22}$-Glp-1(7–36), $Val^8Arg^{22}$-GLP-1(7–36)-amide, $Val^8Arg^{22}$-GLP-1(7–37), $Val^8His^{22}$-GLP-1(7–36)-amide, $Val^8His^{22}$-GLP-1(7–37), $Arg^{26}$-GLP-1(7–37); $Arg^{34}$-GLP-1(7–37); $Lys^{36}$-GLP-1(7–37); $Arg^{26,34}Lys^{36}$-GLP-1(7–37); $Arg^{26,34}$-GLP-1(7–37); $Arg^{26,34}Lys^{40}$-GLP-1(7–37); $Arg^{26}Lys^{36}$-GLP-1(7–37); $Arg^{34}Lys^{36}$-GLP-1(7–37); $Val^8Arg^{22}$-GLP-1(7–37); $Met^8Arg^{22}$-GLP-1(7–37); $Gly^8His^{22}$-GLP-1(7–37); $Val^8His^{22}$-GLP-1(7–37); $Met^8His^{22}$-GLP-1(7–37); $His^{37}$-GLP-1(7–37); $Gly^8$-GLP-1(7–37); $Val^8$-GLP-1(7–37); $Met^8$-GLP-1(7–37); $Gly^8Asp^{22}$-GLP-1(7–37); $Val^8Asp^{22}$-GLP-1(7–37); $Met^8Asp^{22}$-GLP-1(7–37); $Gly^8Glu^{22}$-GLP-1(7–37); $Val^8Glu^{22}$-GLP-1(7–37); $Met^8Glu^{22}$-GLP-1(7–37); $Gly^8Lys^{22}$-GLP-1(7–37); $Val^8Lys^{22}$-GLP-1(7–37); $Met^8Lys^{22}$-GLP-1(7–37); $Gly^8Arg^{22}$-GLP-1(7–37); $Val^8Lys^{22}His^{37}$-GLP-1(7–37); $Gly^8Glu^{22}His^{37}$-GLP-1(7–37); $Val^8Glu^{22}His^{37}$-GLP-1(7–37); $Met^8Glu^{22}His^{37}$-GLP-1(7–37); $Gly^8Lys^{22}His^{37}$-GLP-1(7–37); $Met^8Lys^{22}His^{37}$-GLP-1(7–37); $Gly^8Arg^{22}His^{37}$-GLP-1(7–37); $Val^8Arg^{22}His^{37}$-GLP-1(7–37); $Met^8Arg^{22}His^{37}$-GLP-1(7–37); $Gly^8His^{22}His^{37}$-GLP-1(7–37); $Val^8His^{22}His^{37}$-GLP-1(7–37); $Met^8His^{22}His^{37}$-GLP-1(7–37); $Gly^8His^{37}$-GLP-1(7–37); $Val^8His^{37}$-GLP-1(7–37); $Met^8His^{37}$-GLP-1(7–37); $Gly^8Asp^{22}His^{37}$-GLP-1(7–37); $Val^8Asp^{22}His^{37}$-GLP-1(7–37); $Met^8Asp^{22}His^{37}$-GLP-1(7–37); $Arg^{26}$-GLP-1(7–36)-amide; $Arg^{34}$-GLP-1(7–36)-amide; $Lys^{36}$-GLP-1(7–36)-amide; $Arg^{26,34}Lys^{36}$-GLP-1(7–36)-amide; $Arg^{26,34}$-GLP-1(7–36)-amide; $Arg^{26,34}Lys^{40}$-GLP-1(7–36)-amide; $Arg^{26}Lys^{36}$-GLP-1(7–36)-amide; $Arg^{34}Lys^{36}$-GLP-1(7–36)-amide; $Gly^8$-GLP-1(7–36)-amide; $Val^8$-GLP-1(7–36)-amide; $Met^8$-GLP-1(7–36)-amide; $Gly^8Asp^{22}$-GLP-1(7–36)-amide; $Gly^8Glu^{22}His^{37}$-GLP-1(7–36)-amide; $Val^8Asp^{22}$-GLP-1(7–36)-amide; $Met^8Asp^{22}$-GLP-1(7–36)-amide; $Gly^8Glu^{22}$-GLP-1(7–36)-amide; $Val^8Glu^{22}$-GLP-1(7–36)-amide; $Met^8Glu^{22}$-GLP-1(7–36)-amide; $Gly^8Lys^{22}$-GLP-1(7–36)-amide; $Val^8Lys^{22}$-GLP-1(7–36)-amide; $Met^8Lys^{22}$-GLP-1(7–36)-amide; $Gly^8His^{22}His^{37}$-GLP-1(7–36)-amide; $Gly^8Arg^{22}$-GLP-1(7–36)-amide; $Val^8Arg^{22}$-GLP-1(7–36)-amide; $Met^8Arg^{22}$-GLP-1(7–36)-amide; $Gly^8His^{22}$-GLP-1(7–36)-amide; $Val^8His^{22}$-GLP-1(7–36)-amide; $Met^8His^{22}$-GLP-1(7–36)-amide; $His^{37}$-GLP-1(7–36)-amide; $Val^8Arg^{22}His^{37}$-GLP-1(7–36)-amide; $Met^8Arg^{22}His^{37}$-GLP-1(7–36)-amide; $Gly^8His^{37}$-GLP-1(7–36)-amide; $Val^8His^{37}$-GLP-1(7–36)-amide; $Met^8His^{37}$-GLP-1(7–36)-amide; $Gly^8Asp^{22}$ $His^{37}$-GLP-1(7–36)-amide; $Val^8Asp^{22}His^{37}$-GLP-22-GLP-1(7–36)-amide; $Met^8Asp^{22}His^{37}$-GLP-1(7–36)-amide; $Val^8Glu^{22}His^{37}$-GLP-1(7–36)-amide; $Met^8Glu^{22}His^{37}$-GLP-1(7–36)-amide; $Gly^8Lys^{22}$ $His^{37}$-GLP-1(7–36)-amide; $Val^8Lys^{22}His^{37}$-GLP-1(7–36)-amide; $Met^8Lys^{22}His^{37}$-GLP-1(7–36)-amide; $Gly^8Arg^{22}His^{37}$-GLP-1(7–36)-amide; $Val^8His^{22}His^{37}$-GLP-1(7–36)-amide; $Met^8His^{22}His^{37}$-GLP-1(7–36)-amide; and derivatives thereof.

In another embodiment the antidyslipidemic drug is a statin. In a preferred embodiment the statin is selected from atorvastatin, lovastatin, fluvastatin, simvastatin, pravastatin, rivastatin, itavastatin and ZD-4522.

In yet another embodiment the antidyslipidemic drug is a squalene synthase inhibitor. In a preferred embodiment the squalene synthase inhibitor is selected from YM-53601 and ER-27856.

In a further embodiment the antidyslipidemic drug is a bile acid binding resin. In a preferred embodiment the bile acid binding resin is selected from cholestyramine and cholestipol.

In another embodiment the antidyslipidemic drug is an IBAT inhibitor. In a preferred embodiment the IBAT inhibitor is S-8921.

In yet another embodiment the GLP-1 compound and the other antidyslipidemic drug are co-administered to the patient. The two compounds may be administered as separately formulated compounds or they may be administered as one formulation comprising both compounds. In a further embodiment, the GLP-1 compound is administered in a regimen, which additionally comprises administration of the other antidyslipidemic drug. In a preferred embodiment the GLP-1 compound is a parenteral medicament. In another preferred embodiment the other antidyslipidemic drug is an oral medicament. In yet another embodiment the GLP-1 compound and the other antidyslipidemic drug are administered as a single combined formulation, preferably a parenteral formulation.

In yet another embodiment, the GLP-1 compound and the other antidyslipidemic drug are administered in suboptimal dosages, i.e. dosages lower than the optimal dosages for single compound therapy.

In yet another embodiment, the dosage of said GLP-1 compound is from 0.5 µg/kg/day to 10 µg/kg/day.

In yet another embodiment, the dosage of said GLP-1 compound is from 0.1 µg/kg/day to 1 µg/kg/day.

In a further embodiment the GLP-1 compound and the other antidyslipidemic drug are administered in sufficient amount and for a sufficient time to produce a synergistic effect, preferably for at least 4 weeks.

The subject or patient is preferably a mammal, more preferably a human.

The route of administration may be any route, which effectively transports the active compound to the appropriate or desired site of action, such as oral, nasal, buccal, pulmonal, transdermal or parenteral.

Pharmaceutical compositions (or medicaments) containing a GLP-1 compound, such as $Arg^{34}$, $Lys^{26}(N^{\epsilon}-(\gamma-Glu(N^{\alpha}-hexadecanoyl)))$-GLP-1(7–37), may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of a GLP-1 compound in the form of a nasal or pulmonal spray. As a still further option, the GLP-1 compound can also be administered transdermally, e.g. from a patch, optionally a iontophoretic patch, or transmucosally, e.g. bucally. The above-mentioned possible ways to administer stable derivatives of GLP-1 analogs are not considered as limiting the scope of the invention.

Pharmaceutical compositions containing GLP-1 compounds, such as $Arg^{34}$, $Lys^{26}(N^{\epsilon}-(\gamma-Glu(N^{\alpha}-hexadecanoyl)))$-GLP-1(7–37), may be prepared by conventional techniques, e.g. as described in Remington's *Pharmaceutical Sciences*, 1985 or in Remington: *The Science and Practice of Pharmacy*, $19^{th}$ edition, 1995.

Thus, the injectable compositions of GLP-1 compounds can be prepared using the conventional techniques of the pharmaceutical industry which involves dissolving and mixing the ingredients as appropriate to give the desired end product.

According to one procedure, e.g. $Arg^{34}$, $Lys^{26}(N^{\epsilon}-(\gamma-Glu(N^{\alpha}-hexadecanoyl)))$-GLP-1(7–37) is dissolved in an amount of water which is somewhat less than the final volume of the composition to be prepared. An isotonic agent, a preservative and a buffer are added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Further to the above-mentioned components, solutions containing a GLP-1 compound may also contain a surfactant in order to improve the solubility and/or the stability of the peptide.

According to one embodiment of the present invention, the GLP-1 compound is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 0.1 mg/ml, typically from 0.1 mg/ml to 10 mg/ml, such as from 1 mg/ml to 5 mg/ml of GLP-1 compound.

GLP-1 compounds such as $Arg^{34}$, $Lys^{26}(N^{\epsilon}-(\gamma-Glu(N^{\alpha}-hexadecanoyl)))$-GLP-1(7–37) can be used in the treatment of various diseases. The optimal dose level for any patient (effective amount) will depend on the disease to be treated and on a variety of factors including the efficacy of the specific GLP-1 compound employed, the age, body weight, physical activity, and diet of the patient, on a possible combination with other drugs, and on the severity of the case.

Pharmaceutical compositions (or medicaments) containing an antidyslipidemic drug, such as a statin, a squalene synthase inhibitor, a bile acid binding resin or an IBAT inhibitor, may be administered by suitable dosage forms such as oral, nasal, pulmonal, buccal or transdermal to patients in need of such a treatment. The preferred route of administration of said antidyslipidemic drug is orally. Pharmaceutical compositions containing an antidyslipidemic drug may be prepared by conventional techniques, e.g. as described in Remington: The Science and Practice of Pharmacy, 19th Edition, Gennaro, Ed., Mack Publishing Co., Easton, Pa., 1995.

Typical compositions of antidyslipidemic drugs, e.g. a statin, a squalene synthase inhibitor, a bile acid binding resin or an IBAT inhibitor, include a crystalline compound of the present invention associated with a pharmaceutically acceptable excipient, which may be a carrier or a diluent or be diluted by a carrier, or enclosed within a carrier, which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier, which may be in the form of a ampoule, capsule, sachet, paper, or other container. When the carrier serves as a diluent, it may be solid, semi-solid, or liquid material, which acts as a vehicle, excipient, or medium for the active compound. The active compound can be adsorbed on a granular solid container for example in a sachet. Some examples of suitable carriers are water, salt solutions, alcohol's, polyethylene glycol's, polyhydroxyethoxylated castor oil, peanut oil, olive oil, gelatine, lactose, terra alba, sucrose, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compound.

If a solid carrier is used for oral administration, the preparation may be tabletted, placed in a hard gelatine capsule in powder or pellet form or it can be in the form of a troche or lozenge. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain the compound of the present invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet of an antidyslipidemic drug, which may be prepared by conventional tabletting techniques, may contain:

| Core: | |
|---|---|
| Active compound | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

Antidyslipidemic drugs are effective over a wide dosage range. For example, in the treatment of adult humans, dosages from 0.01 mg/day to 10 mg/day, preferably from 0.1 mg/day to 3 mg/day may be used. A most preferable dosage is less than 2 mg/day. In choosing a regimen for patients it may frequently be necessary to begin with a dosage of from about 2 to about 10 mg per day and when the condition is under control to reduce the dosage as low as from about 0.01 to about 3 mg per day. The exact dosage will depend upon the mode of administration, on the therapy desired, the administration form, the subject to be treated and the body weight of the subject to be treated.

Generally, the antidyslipidemic drugs of the present invention are dispensed in unit dosage form comprising from about 0.01 to about 10 mg of active ingredient together with a pharmaceutically acceptable carrier per unit dosage.

Usually, dosage forms suitable for oral, nasal, pulmonary or transdermal administration comprise from about 0.01 mg to about 10 mg, preferably from about 0.1 mg to about 3 mg of the compound of the invention admixed with a pharmaceutically acceptable carrier or diluent.

Irrespective of the dosage forms for the GLP-1 compound and for the other antidyslipidemic drug, they may advantageously be supplied as a kit for treatment of dyslipidemia, hyperlipoproteinemia, hypertriglyceridemia, hyperlipidemia or hypercholesterolemia. The kit may contain a single dosage form or it may contain two dosage forms, i.e. one for each compound to be administered.

In one embodiment the dosage of said GLP-1 compound is from 0.5 $\mu$g/kg/day to 10 $\mu$g/kg/day, and the dosage of said antidyslipidemic drug is from 0.01 mg/day to 10 mg/day. In another embodiment the dosage of said GLP-1 compound is from 0.1 $\mu$g/kg/day to 1 $\mu$g/kg/day, and the dosage of said antidyslipidemic drug is from 0.01 mg/day to 10 mg/day. In another embodiment the dosage of said GLP-1 compound is from 0.5 $\mu$g/kg/day to 10 $\mu$g/kg/day, and the dosage of said antidyslipidemic drug is from 0.1 mg/day to 3 mg/day In another embodiment the dosage of said GLP-1 compound is from 0.1 $\mu$g/kg/day to 1 $\mu$g/kg/day, and the dosage of said antidyslipidemic drug is from 0.1 mg/day to 3 mg/day. In another embodiment the dosage of said GLP-1 compound is from 0.1 $\mu$g/kg/day to 1 $\mu$g/kg/day, and the dosage of said antidyslipidemic drug is from 0.2 mg/day to 2 mg/day.

The combined treatment with a GLP-1 compound and another antidyslipidemic drug may also be combined with a third or more further pharmacologically active Substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, GLP-1 agonists, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the $\beta$-cells; Cholestyramine, colestipol, clofibrate, gemfibrozil, lovastatin, pravastatin, simvastatin, probucol, dextrothyroxine, neteglinide, repaglinide; $\beta$-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and $\alpha$-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, $\beta$3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR $\beta$ agonists; histamine H3 antagonists.

It should be understood that any suitable combination of the compounds according to the invention with one or more of the above-mentioned compounds and optionally one or more further pharmacologically active substances are considered to be within the scope of the present invention.

EXAMPLES

Test of Efficacy of Combined Use of GLP-1 and Another Drug for Treating Dyslipidemia
Patients
Dyslipidemic Type 2 diabetes patients are randomized to match body weigth, LDL and $HbA_{1C}$ levels before start of study. All patients have any antidiabetic medication discontinued for at least two weeks before start of study.
Dosing Groups
  1) Control, dosed with both vehicles
  2) GLP-1 (or $Arg^{34}$, $Lys^{26}(N^{\epsilon}\text{-}(\gamma\text{-}Glu(N^{\alpha}\text{-}hexa\text{-}decanoyl)))\text{-}GLP\text{-}1(7\text{--}37)$)+vehicle
  3) Vehicle+statin/fibric acid derivative
  4) GLP-1 (or $Arg^{34}$, $Lys^{26}(N^{\epsilon}\text{-}(\gamma\text{-}Glu(N^{\alpha}\text{-}hexa\text{-}decanoyl)))\text{-}GLP\text{-}1(7\text{--}37)$)+statin/fibric acid derivative
Statins: Atorvastatin, lovastatin, fluvastatin, simvastatin, pravastatin, rivastatin, itavastatin or ZD-4522
Fibric acid derivatives: YM-53601 or ER-27856
Patients are dosed for 4 weeks (dosing according to kinetics of chosen compounds). Doses of both GLP-1 and statin/fibric acid derivative are chosen slightly lower than what is needed for optimal treatment of dyslipidemia with monotherapy to enable detection of synergistic or additive effect in group 4.
Experimental Set-up
  Before the first dose and on day 14 and 28 blood samples are obtained from fasted subjects and plasma levels of glycerol, triglycerides, FFA, glucose, $HbA_{1c}$, fructosamine, C-peptide and glucagon are measured. Additionally, a detailed NMR profile of lipoproteins with subclasses of LDL, HDL, VLDL is performed (Lipomed,). Furthermore, on day 28 a lipid tolerance test is performed and levels of LDL, HDL, VLDL, triglycerides, FFA, glucose, C-peptide and glucagon are measured every 60 minutes from 0 to 8 hours. To evaluate the effect on hypertension of correcting dyslipidemia, blood pressure is measured before first dose and on day 14 and 28.
Evaluation of Results
Synergistic effect of GLP-1 and statin/fibric acid derivative treatment is shown by correction of dyslipidemia in group 4 being more pronounced than the sum of effects in group 2 or 3. Additive effect of GLP-1 and statin/fibric acid derivative treatment is shown by correction of dyslipidemia in group 4 being more pronounced than in group 2 or 3.

What is claimed is:

1. A method for treating dyslipidemia in a patient, said method comprising administering to a patient in need of such treatment an effective amount of an anolog of exendin-4 that has one or more amino acids inserted at the C-terminus of exendin-4 and an effective amount of a squalene synthase inhibitor.

2. A method for treating dyslipidemia in a patient, said method comprising administering to a patient in need of such treatment an effective amount of an analog of exendin-4 that has one or more amino acids inserted at the C-terminus of exendin-4 and an effective amount of an ileal bile acid co-transporter (IBAT) inhibitor.

* * * * *